United States Patent
McKinney

(10) Patent No.: US 6,365,152 B1
(45) Date of Patent: Apr. 2, 2002

(54) SCOURS TREATMENT AND METHOD OF MAKING SAME

(75) Inventor: Randy R. McKinney, Grangeville, ID (US)

(73) Assignee: Bovine Health Products, Inc., Grangeville, ID (US)

(*) Notice: Subject to any disclaimer, the term of this patent is extended or adjusted under 35 U.S.C. 154(b) by 0 days.

(21) Appl. No.: 09/809,596

(22) Filed: Mar. 15, 2001

(51) Int. Cl.$^7$ ................................. A01N 63/00
(52) U.S. Cl. .................. 424/93.4; 424/93.45; 424/617; 424/780; 435/252.1; 435/252.9
(58) Field of Search ................. 424/93.4, 725, 424/93.45, 780, 617; 435/252.1, 252.9

(56) References Cited

U.S. PATENT DOCUMENTS

| | | |
|---|---|---|
| 4,164,568 A | 8/1979 | Bywater |
| 4,762,822 A | 8/1988 | Ettinger |
| 4,839,347 A | 6/1989 | Franz |
| 4,945,085 A | 7/1990 | Steiner |
| 5,008,248 A | 4/1991 | Bywater et al. |
| 5,028,437 A | 7/1991 | Jerrett |
| 5,095,008 A | 3/1992 | Pflaumer et al. |
| 5,182,112 A | 1/1993 | Kurazumi et al. |
| 5,614,501 A | 3/1997 | Richards |
| 5,858,356 A * | 1/1999 | Wolf et al. |
| 5,902,578 A * | 5/1999 | Halpin-Dohnalek et al. |
| 6,066,341 A | 5/2000 | Wilson |

* cited by examiner

*Primary Examiner*—Leon B. Lankford, Jr.
(74) *Attorney, Agent, or Firm*—Richard D. Clarke

(57) ABSTRACT

A new and improved formulation and method for making same, for a treatment for scours in farm animals is provided. More particularly, the present invention relates to a treatment which enables rapid relief of symptoms in an affected animal with a mortality of 1% or less by providing trace organic minerals in microgram quantities which act as nutrients for the animal. The treatment provides further nutritional requirements in the form of vitamin A, folic acid and vitamin $D_3$ supplements, cobalt amino acid chelates and dried kelp, a source of minerals, amino acids, simple and complex carbohydrates, iodine and fiber. In addition, a bacterial innoculum consisting of Acidophilus species is introduced which would inhibit growth of pathogenic or opportunistic species of bacteria by competition for nutrients as well as providing for required vitamins as a by-product of metabolism.

20 Claims, No Drawings

SCOURS TREATMENT AND METHOD OF MAKING SAME

BACKGROUND OF THE INVENTION

1. Field of the Invention

The present invention relates to a new and improved scours treatment for young animals and method of using it. More particularly, the present invention relates to a composition composed of two groups of compounds, when combined and properly administered to young animals suffering from diarrhea, infectious diarrhea, scours and dehydration, acts to rapidly relieve the symptoms associated with the disease. The compounds utilized in the two groups radically depart from conventional treatments.

2. Description of the Related Art

Cattle are a major source of protein and wealth in a major portion of the world today. With a number of third world countries struggling to feed a growing number of impoverished people, affordable, efficient treatments for common diseases of cattle are becoming increasingly important.

Calf scours complex is a worldwide malady affecting calves ranging from birth to three weeks of age with a high mortality rate in untreated cases. Dairy calves are weaned at 3 weeks to 90 days. At the time of weaning, young calves are stressed by the change in diet and other conditions. A significant percentage of calves develop diarrhea, a condition generally referred to as scours. Even in treated calves, there is still an unacceptably high rate of mortality. The loss of young livestock to this cause is a substantial burden to the livestock industry worldwide.

The disease agents are primarily Reovirus and Coronavirus with colibacillosis and Cryptosporidium sp. as contributing factors. *Escherichia coli* is also a major cause of infectious scours in calves. In addition, Salmonella sp. and Clostridium sp. groups have been found associated with outbreaks outside of North America.

Currently, a reovirus vaccine is available and an experimental Coronavirus vaccine may become available for prevention. Treatments consisting of antibiotics are used in virtually all infected herds, even when isolation of infected animals is or is not possible, or in cases where isolation has proven to be ineffective in preventing spread. Often treatment of scours with antibiotics has proven to be slow or even ineffectual. In addition, the withdrawal times required for animals may be lengthy and these antibiotic treatments are relatively expensive to administer.

The lack of response of infectious diarrhea to antibiotic treatment may be attributable to the development of resistant strains of bacteria. In addition, infection by multiple agents causing similar symptoms might render such treatments ineffective. Results from diagnostic laboratories have indicated that several etiologic agents can be simultaneously associated with one afflicted animal. In one particular case, a single bovine fecal sample tested positive for *E. coli*, Cryptosporidium and Rotavirus. This type of multiple etiology would make any antibiotic treatment for infectious diarrhea or white scours ineffective.

The benefits of nutritional compound formulations designed for ameliorating the symptoms of the disease are well known. Examples of different types and kinds of compositions and techniques for treatment of symptoms of calf scours are disclosed in U.S. Pat. Nos. 6,066,341, 5,614,501, 5,028,437 and 5,009,248.

In general, the currently used compositions used for treatment of symptoms of calf diarrhea contain one or more of the following ingredients: psyllium, amino acids, electrolytes, citrate, and complex carbohydrates. This is especially the case in preparations containing primarily electrolytes for hydration therapy. Such components are found to be useful due to the ease of storage in dry states and convenience of use when re-hydrated.

The use of glucose and electrolytes helps to reverse the effects of dehydration in affected animals. Fibrous components such as psyllium act as a water binding swelling agent in the intestines and reportedly carries with it a lactose decomposing enzyme. Amino acids such as glycine and citrate salts are added to improve palatability, ease of formulation and stability of the compounds.

The reported efficacy of these treatments vary and the mortality rate for the treatments can vary from 4% to 25% depending on the treatment used. Mortality rates in general can range as high as 50%.

Treatments for symptoms of scours in calves are known in the prior art. Such a treatment is described in U.S. Pat. No. 6,066,341. This inventive formulation includes fiber, electrolytes and three energy sources. These energy sources are sugar, medium chain triglycerides and glycine.

This novel invention, while allowing for rehydration of affected animals as well as providing an energy source, does little to fulfill the total nutritional requirements of the animals during the dosing procedure, thus utilizing the treatment period to reverse critical weight loss from nutritional deficiency.

The reported mortality of infected animals after administration of the treatment ranges from 3.4% up to 21.2%. It would be highly desirable to have a treatment with a significantly lower after treatment mortality rate.

The invention does provide for a water binding swelling agent in the intestines but does not provide for any beneficial micro-organisms to recolonize the infected intestinal tract to provide for needed vitamin and nutritional needs as soon as possible. In addition, the introduced bacteria would effectively compete with pathogenic organisms that might be present.

Therefore, it would be highly desirable to have a new and improved formulation and method for using same for a calf scours treatment which would allow rapid relief from the symptoms of diarrhea by providing a more complete nutritional regimen to reverse the effects of malnutrition resulting in 1% or less mortality post treatment and introduce beneficial micro-organisms to recolonize the affected intestinal tract in order to provide for needed vitamin and nutritional needs of the animal and provide a bacterial population that would effectively compete with pathogenic organisms which may still be present.

The treatment described in U.S. Pat. No. 5,614,501 addresses the problem of providing for a method of decreasing the amount of harmful bacteria present in the gastrointestinal tract by incorporating polyphenols in the composition. Additionally, the composition provides for hemicelluloses which are preferably used as a nutritional source for beneficial bacteria in the gastrointestinal tract. However, in many cases, the populations of beneficial microorganisms is severely depleted. No provisions have been made in this formulation to innoculate the infected gastrointestinal tract with beneficial microorganisms.

Therefore, it would be highly desirable to have a new and improved formulation and method for using same for a calf scours treatment which would allow rapid relief from the symptoms of diarrhea by providing a more complete nutritional regimen to reverse the effects of malnutrition and introduce beneficial micro-organisms to recolonize the affected intestinal tract in order to provide for needed vitamin and nutritional needs of the animal and provide a bacterial population that would effectively compete with pathogenic organisms which may still be present.

U.S. Pat. No. 5,028,437 describes a treatment that addresses the problem of providing for an energy source in the form of carbohydrates, electrolytes and chloride ions. However, the treatment does not address the total nutritional requirements of the animal during the treatment period when milk is withheld. When using the scours treatment that is the subject of this patent application, there is no need to withhold milk from calves during the treatment period, as is the case here for U.S. Pat. No. 5,028,437.

Therefore, it would be highly desirable to have a new and improved formulation and method for using same for a calf scours treatment which would allow rapid relief from the symptoms of diarrhea by providing a more complete nutritional regimen to reverse the effects of malnutrition and introduce beneficial micro-organisms to recolonize the affected intestinal tract in order to provide for needed vitamin and nutritional needs of the animal and provide a bacterial population that would effectively compete with pathogenic organisms which may still be present.

U.S. Pat. No. 5,009,248 describes a treatment that has an energy source in the form on mono-saccharides, amino acids, citric acid and electrolytes for the purpose of redydration of an animal suffering the effects of dehydration due to the effects of diarrhea. While this does address the immediate and probably most severe symptom of the disease, it again does not provide more complete nutritional needs of the animal or any innoculum to reintroduce beneficial bacteria to recolonize the gastrointestinal tract.

Therefore, it would be highly desirable to have a new and improved formulation and method for using same for a calf scours treatment which would allow rapid relief from the symptoms of diarrhea by providing a more complete nutritional regimen to reverse the effects of malnutrition and introduce beneficial micro-organisms to recolonize the affected intestinal tract in order to provide for needed vitamin and nutritional needs of the animal and provide a bacterial population that would effectively compete with pathogenic organisms which may still be present.

Finally, U.S. Pat. No. 4,164,568 provides for a treatment for scours composed of a monosaccaride, amino acids and citric acid. Again, while this treatment attempts to address the immediate and probably most severe symptom of the disease, namely dehydration, this treatment, like others before it, again does not provide for the more complete immediate nutritional needs of the animal or any innoculum to reintroduce beneficial bacteria to recolonize the gastrointestinal tract.

Therefore, it would be highly desirable to have a new and improved formulation and method for using same for a calf scours treatment which would allow rapid relief from the symptoms of diarrhea by providing a more complete nutritional regimen to reverse the effects of malnutrition resulting in 1% or less mortality post treatment and introduce beneficial micro-organisms to recolonize the affected intestinal tract in order to provide for needed vitamin and nutritional needs of the animal and provide a bacterial population that would effectively compete with pathogenic organisms which may still be present.

SUMMARY OF THE INVENTION

Therefore, the principal object of the present invention is to provide a new and improved formulation and method for using same, for a treatment for infectious diarrhea, scours and the accompanying dehydration symptoms in farm animals.

It is a further object of the present invention to provide such a new and improved formulation and method for using same, for a treatment for scours in farm animals with a greater efficacy than current treatments. Studies have shown that the proposed treatment results in a 1% or less mortality rate among infected animals.

It is a further object of the present invention to provide such a new and improved formulation and method for using same, for a treatment for scours in farm animals with a more complete nutritional supplement to combat the effects of malnutrition in the affected animal resulting in 1% or less mortality in infected animals post treatment. Specifically, the formulation contains dried kelp, folic acid, vitamin A supplements, vitamin D3 supplement, and cobalt amino acid chelates.

It is a further object of the present invention to provide such a new and improved formulation and method for using same, for a treatment for scours in farm animals, which would introduce beneficial bacterial populations to recolonize the gastrointestinal tract of affected animals. The bacteria introduced would compete with pathogenic or opportunistic bacteria and would provide necessary nutrients as by-products to the affected animals.

It is yet a further object of the present invention to provide such a new and improved formulation and method for using same, for a treatment for scours in farm animals, which would be inexpensive to manufacture, ship and store and which provides relief from symptoms to the affected animal very rapidly upon application. The formulation of the treatment provides a simple, yet effective means by which to treat infected animals.

Briefly, the above and further objects of the present invention are realized by providing a new and improved formulation and method for using same, for a treatment for scours in farm animals. More particularly, the present invention relates to a treatment which enables rapid relief of symptoms in an affected animal with a mortality of 1% or less by providing trace organic minerals in microgram quantities which act as nutrients for the animal. The treatment provides further nutritional requirements in the form of vitamin A, folic acid and vitamin $D_3$ supplements, cobalt amino acid chelates and dried kelp, a source of minerals, amino acids, simple and complex carbohydrates, iodine and fiber. In addition, a bacterial innoculum consisting of Acidophilus species is introduced which would inhibit growth of pathogenic or opportunistic species of bacteria by competition for nutrients as well as providing for required vitamins as a by-product of metabolism.

DESCRIPTION OF THE PREFERRED EMBODIMENT

The calf scours treatment of the present invention is comprised in a liquid state of trace minerals, cobalt amino acid chelates, Acidophilus sp., kelp and vitamins in a solution using distilled water as the carrier.

Trace mineral elements have been linked to immune system health, cell growth enhancement, glucose tolerance factor and other overall health concerns. The above mentioned trace elements, when combined in the current formulation have an unexpected synergy in treatment of a severely nutritionally compromised animal.

The second solution used to formulate the new treatment composition is composed of a bacterial species that would recolonize the gastrointestinal tract as well as a nutritional formulation to provide needed vitamins and minerals to the affected animal. In addition, kelp, a natural source of carbohydrates, amino acids, vitamins, minerals and trace elements is also added. Kelp contains over 60 minerals and elements including iodine, 21 amino acids, simple and complex carbohydrates. It is believed to be a promoter of glandular health, especially for the pituitary, adrenal and thyroid glands. The thyroid and pituitary glands regulate certain functions of digestion. In addition, kelp provides a natural source of fiber.

After the two solutions are mixed, an oral dose of approximately 10–15 ml. of the resultant treatment solution is administered to the affected animal. The dose is repeated every 24 hours until symptoms are relieved. After the animal responds to the treatment, and regains its appetite, a regular diet and feeding schedule can be resumed. Furthermore, with the instant scours treatment composition and method, there is no requirement for withholding milk from the calves, and there is no requirement that a feeding calf be taken off feed during the treatment period.

The present composition was administered on the above-noted 24 hour cycle to several test groups of infected animals. Control group calves were treated with the standard protocol of each dairy or cattle ranch. This protocol consisted of one or more of the following: antibiotics, electrolytes orally, and scour boluses. In severe cases, lactated Ringers Solution was administered intravenously. These extreme cases had been on drug therapy prior to the start of testing with the present scours treatment and method. Mortality rate among the control calf group, those receiving the standard protocol treatment, ranged from 20 to 30%. Mortality among those animals treated with the present scours treatment composition was 1% or less. Affected animals that were treated with the present composition were asymptomatic after 1 or 2 treatments. The treated calves displayed bright eyes, vigorous behavior, healthy appetites and shiny coats.

EXAMPLE 1

A field trial was conducted where 26 calves were treated with a protocol of penicillin, electrolytes orally, and scour boluses. The antibiotic treated group suffered a 30% mortality rate.

Furthermore, calves on the drug therapy were lethargic, had dull rough coats, glassy eyes and poor appetite with runny stools in some cases. Often, these conditions were still present even after more than two weeks of treatments.

A second group of 48 calves were given the present composition. The group given the new formulation sustained a 1% mortality rate. Among the second group, several had been given the antibiotic treatment and were not responding, so they were treated with the present composition. It was evident that those calves which had previously been administered antibiotics and subsequently treated with the new formulation were slower to respond to the new treatment than those affected animals which had not previously been administered antibiotics.

Moreover, calves treated with only the present composition had bright eyes, shiny coats, vigor and healthy appetites. The animals in the scours treatment test group that were administered the present composition, rapidly became asymptomatic following treatment. Agin, the treated calves displayed bright eyes, increased vigor, healthy appetites and shiny coats.

EXAMPLE 2

A second field trial included 10 calves that were treated with sulfamethazine tablets and LA 200 injections. These calves were also lethargic, had dull and glassy eyes, poor appetites, dull rough coats and some had runny stools even after weeks of treatment.

Thirty one calves received the present composition in doses of 15 to 30 ml in 24 hour intervals. These calves were asymptomatic after 1 or 2 doses and again had bright eyes, shiny coats, good appetites and increased vigor.

EXAMPLE 3

A third field trial was conducted at a dairy that had a history of problems with scours. For several years, this dairy had stopped raising calves due to its 98 to 100% mortality rate.

Efforts to address the problem included excavation of soil from each calf pen, sterilization of the ground and facilities and replacement of soil each time calves were changed in a pen. The dairy had consistently used veterinarians to treat infected animals in an effort to reduce mortality.

After the dairy began raising calves again, the mortality rate among the calves due to the effects of scours was 90%. Typically, sick milking cows are kept in a "hospital pen" dosed with high levels of antibiotics, and the resulting "hospital milk" fed to afflicted calves so that the several different antibiotics given to the milking cow is passed on to the affected calves through the antibiotic laced milk. This is a common practice in many dairy herd operations.

The calves in the test group that were administered the present scours treatment composition were placed on "milk replacer" rather than fed the antibiotic laced "hospital milk" from the "hospital pen cows." This group again responded favorably in a similar manner to the previous studies following treatment.

After several days, it became evident that all of the calves treated with the dairy's standard protocol antibiotic treatment were very ill and would very likely die. The present compound was then administered to this group as well in an effort to save the animals. The calves that had been on the antibiotic therapy were slower to respond to the present compound than the animals that had not received the antibiotic therapy. However, after administration of the present compound, mortality in this test group dropped to zero as well.

In this study, one calf in particular was worthy of special note. The calf had been on antibiotic therapy for several days. The animal was down and too weak to stand unassisted. Fifteen milliliters (ml) of the present scour treatment composition was administered the first day. The stool was watery and green. The animal had poor hydration and was too weak to stand.

On the second day, a watery yellow colored stool was noted. Again, the calf was given 15 ml of the present composition and lactated Ringer's solution subcutaneously.

After the third day of treatment, the stool was loose and green, the calf had fair hydration and was up and moving around in a much improved condition. The present composition was administered again on this day in a 15 ml dosage.

On the fourth day, the overall condition of the affected animal was good. The stool was firm and green in color and none of the present composition was administered. The calf recovered fully, with bright eyes, shiny coat, increased vigor and a normal healthy appetite.

The calf scours treatment of the present invention is comprised in a liquid state of 22 constituents. These constituents are formulated in two liquid solutions which are then combined and stored in liquid form. The composition is readily available in this form for administration to the animal at 10–15 ml per dose most commonly at 24 hour intervals.

The first solution is composed of trace minerals in microgram amounts. The following is a list of trace minerals with the approximate percentage of total trace minerals in solution:

| | |
|---|---|
| Cobalt | 19% |
| Copper | 19% |
| Silicon | 11.5% |
| Neodymium | 9.5% |
| Praseodymium | 9.5% |
| Nickel | 6.7% |
| Chlorine | 6.2% |
| Zinc | 5.9% |
| Yttrium | 5.7% |
| Strontium | 1.4% |
| Titanium | 1.4% |
| Aluminum | 1.4% |
| Chromium | 0.95% |
| Gallium | 0.95% |
| Rubidium | 0.95% |
| Trace minerals | 100% |

The trace organic minerals are suspended in a liquid carrier prior to final formulation of the new treatment composition.

The following are the constituents of the second solution:

| | |
|---|---|
| *Acidophilus sp.* | 3.0 grams |
| Water (distilled) | 1.0 liquid ounce |
| Dried kelp | 1.0 gram |
| Folic acid | 1.0 gram |
| Vitamin A supplement | 0.5 grams |
| Vitamin D$_3$ supplement | 0.5 grams |
| Cobalt amino acid chelates | 0.2 grams |

All ingredients are mechanically mixed to form the liquid composition which may then be administered orally to affected animals in doses of 10 to 15 ml. A needle-less syringe is used to administer the required dosage into the back of the affected animals mouth. This treatment is repeated every 24 hours as needed. In severe cases, the dosage can be increased to 15 to 30 ml every 24 hours until the afflicted animal is asymptomatic.

It should be understood, however, that even though these numerous characteristics and advantages of the invention have been set forth in the foregoing description, together with details of the composition and method of application of the invention, the disclosure is illustrative only, and changes may be made in detail, especially in matters of chemistry, dosage and implementation within the principal of the invention to the full extent indicated by the broad general meaning of the terms in which the appended claims are expressed.

What is claimed is:

1. A scours treatment for use in animals comprising:
   (a) a trace minerals solution containing organic mineral elements;
   (b) an Acidophilus sp. innoculum;
   (c) a vitamin solution containing vitamin A, vitamin D, and folic acid;
   (d) cobalt amino acid chelates; and
   (e) dried kelp, whereby said trace minerals solution is added in one part, and said Acidophilus sp. innoculum, vitamin solution, cobalt amino acid chelates and dried kelp are mixed in one ounce of distilled water and is added in two parts.

2. The scours treatment for use in animals according to claim 1, wherein said trace minerals solution containing organic minerals includes about 19% cobalt, about 19% copper, about 11.5% silicon, about 9.5% neodymium, and about 9.5% praseodymium.

3. The scours treatment for use in animals according to claim 2, wherein said trace minerals solution containing organic minerals further includes about 6.7% nickel, about 6.2% chorine, about 5.9% zinc and about 5.7% yttrium.

4. The scours treatment for use in animals according to claim 3, wherein said trace minerals solution containing organic minerals further includes about 1.4% strontium, about 1.4% titanium, and about 1.4% aluminum.

5. The scours treatment for use in animals according to claim 4, wherein said trace minerals solution containing organic minerals further includes about 0.95% chromium, about 0.95% gallium and about 0.95% rubidium.

6. The scours treatment for use in animals according to claim 1, wherein said Acidophilus sp. innoculum is added in about 3 grams per about one ounce of distilled water.

7. The scours treatment for use in animals according to claim 1, wherein said vitamin solution containing vitamin A, vitamin D, and folic acid includes about 1 gram of folic acid, about 0.5 grams of vitamin A, and about 0.5 grams of vitamin D added to about one ounce of distilled water.

8. The scours treatment for use in animals according to claim 1, wherein said cobalt amino acid chelates is added in about 0.2 grams per about one ounce of distilled water.

9. The scours treatment for use in animals according to claim 1, wherein said dried kelp is added in about one gram to about one ounce of distilled water.

10. A method of making a scours treatment compound for animals, comprising the steps:
    (a) providing a trace minerals solution containing organic mineral elements;
    (b) providing an Acidophilus innoculum;
    (c) providing a vitamin solution containing vitamin A, vitamin D, and folic acid;
    (d) providing cobalt amino acid chelates; and
    (e) providing dried kelp, whereby said Acidophilus innoculum, vitamin solution, cobalt amino acid chelates and dried kelp are mixed together prior to mixing with said trace minerals solution; and
    (f) mixing said trace minerals solution added in one part with, and said Acidophilus sp. innoculum, vitamin solution, cobalt amino acid chelates and dried kelp added in two parts, to complete the formulation of said scours treatment compound.

11. The method according to claim 10, wherein said step of providing a trace minerals solution containing organic mineral elements further includes the step of providing a trace minerals solution containing about 19% cobalt, about 19% copper, about 11.5% silicon, about 9.5% neodymium, and about 9.5% praseodymium.

12. The method according to claim 11, wherein said step of providing a trace minerals solution containing organic mineral elements further includes the step of providing a trace minerals solution containing about 6.7% nickel, about 6.2% chorine, about 5.9% zinc and about 5.7% yttrium.

13. The method according to claim 12, wherein said step of providing a trace minerals solution containing organic mineral elements further includes the step of providing a trace minerals solution containing about 1.4% strontium, about 1.4% titanium, and about 1.4% aluminum.

14. The method according to claim 13, wherein said step of providing a trace minerals solution containing organic mineral elements further includes the step of providing a trace minerals solution containing about 0.95% chromium, about 0.95% gallium and about 0.95% rubidium.

15. The method according to claim 13, wherein said step of providing an Acidophilus innoculum, includes the step of providing an Acidophilus innoculum in the concentration of about 3 grams in about one ounce of distilled water.

16. The method according to claim 13, wherein said step of providing a vitamin solution containing vitamin A, vitamin D, and folic acid, includes the step of providing a vitamin solution containing vitamin A, vitamin D, and folic acid in a concentration of about one gram folic acid, about 0.5 grams vitamin A, and about 0.5 grams vitamin D in about one ounce of distilled water.

17. The method according to claim 13, wherein said step of providing cobalt amino acid chelates, includes the step of providing cobalt amino acid chelates in the concentration of about 0.2 grams in about one ounce of distilled water.

18. The method according to claim 13, wherein said step of providing dried kelp includes the step of providing dried kelp in the concentration fo about one gram of dried kelp in about one ounce of distilled water.

19. A method for treating animals afflicted with scours using the scours treatment compound according to claim 1, comprising the steps of:

(a) administering the scours treatment compound in oral doses of about 10 to about 15 milliliters per animal per 24 hour period until the animal is asymptomatic.

20. The method of treating animal afflicted with scours according to claim 19, wherein said step of administering said scours treatment compound includes administering about 15 to about 30 milliliters per animal per 24 hour period for three days in severe cases of acute diarrhea and dehydration.

* * * * *